US00PP26484P2

(12) United States Plant Patent
Beekenkamp

(10) Patent No.: US PP26,484 P2
(45) Date of Patent: Mar. 8, 2016

(54) ***CAMPANULA* PLANT NAMED 'BKPCMPJY'**

(50) Latin Name: *Campanula portenschlagiana*
Varietal Denomination: Bkpcmpjy

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 229 days.

(21) Appl. No.: 13/998,705

(22) Filed: Nov. 26, 2013

(51) Int. Cl.
*A01H 5/02* (2006.01)

(52) U.S. Cl.
USPC ..... Plt./414

(58) Field of Classification Search
USPC ..... Plt./414
See application file for complete search history.

(56) References Cited

PUBLICATIONS

UPOV hit, QZ PBR 2013270, *Campanula portenschlagiana,* published Aug. 16, 2013.*

* cited by examiner

*Primary Examiner* — Anne Grunberg
(74) *Attorney, Agent, or Firm* — C. A. Whealy

(57) ABSTRACT

A new and distinct cultivar of *Campanula* plant named 'Bkpcmpjy' characterized by its upright to outwardly spreading plant habit; freely branching habit; early and freely flowering habit; campanulate-shaped flowers with bright purple violet-colored petals; and good garden performance.

2 Drawing Sheets

Botanical designation: *Campanula portenschlagiana.*
Cultivar denomination: 'BKPCMPJY'.

BACKGROUND OF THE INVENTION

The present invention relates to a new and distinct cultivar of *Campanula* plant, botanically known as *Campanula portenschlagiana*, commonly known as Dalmatian Bellflower and hereinafter referred to by the name 'Bkpcmpjy'.

The new *Campanula* is a product of a planned breeding program conducted by the Inventor in Maasdijk, The Netherlands. The objective of the breeding program is to create new freely flowering *Campanula* plants with attractive flowers and good interior and garden performance.

The new *Campanula* plant originated from a cross-pollination conducted by the Inventor in Maasdijk, The Netherlands in June, 2008 of a proprietary selection of *Campanula portenschlagiana* identified as code number 4400102, not patented, as the female, or seed, parent with a proprietary selection of *Campanula portenschlagiana* identified as code number 4400293, not patented, as the male, or pollen, parent. The new *Campanula* plant was discovered and selected by the Inventor as a single flowering plant from within the progeny of the stated cross-pollination grown in a controlled outdoor nursery in Maasdijk, The Netherlands in June, 2009.

Asexual reproduction of the new *Campanula* plant by cuttings in Maasdijk, The Netherlands, since February, 2010 has shown that the unique features of this new *Campanula* plant are stable and reproduced true to type in successive generations.

SUMMARY OF THE INVENTION

Plants of the new *Campanula* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bkpcmpjy'. These characteristics in combination distinguish 'Bkpcmpjy' as a new and distinct *Campanula* plant:

1. Upright to outwardly spreading plant habit.
2. Freely branching habit.
3. Early and freely flowering habit.
4. Campanulate-shaped flowers with bright purple violet-colored petals.
5. Good garden performance.

Plants of the new *Campanula* differ from plants of the female parent selection in the following characteristics:

1. Plants of the new *Campanula* are broader than plants of the female parent selection.
2. Plants of the new *Campanula* flower earlier than plants of the female parent selection.
3. Plants of the new *Campanula* have larger leaves than plants of the female parent selection.

Plants of the new *Campanula* differ from plants of the male parent selection in the following characteristics:

1. Plants of the new *Campanula* have smaller and darker green-colored leaves than plants of the male parent selection.
2. Plants of the new *Campanula* and the male parent selection differ in flower color as plants of the male parent selection have pale blue-colored flowers.

Plants of the new *Campanula* can be compared to plants of *Campanula portenschlagiana* 'PKMp01', disclosed in U.S. Plant Pat. No. 17,205. Plants of the new *Campanula* differ primarily from plants of 'PKMp01' in the following characteristics:

1. Plants of the new *Campanula* are broader than plants of 'PKMp01'.
2. Plants of the new *Campanula* have larger leaves than plants of 'PKMp01'.
3. Plants of the new *Campanula* flower earlier than plants of 'PKMp01'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the colors of the new *Campanula* plant.

The photograph on the first sheet is a side perspective view of a typical flowering plant of 'Bkpcmpjy' grown in a container.

The photograph on the second sheet is a close-up view of a typical flowering plant of 'Bkpcmpjy'.

DETAILED BOTANICAL DESCRIPTION

Plants used for the aforementioned photographs and following description were grown in 12-cm containers during the early summer in a glass-covered greenhouse in Maasdijk, The Netherlands and under cultural practices typical of commercial production conditions. During the production of the plants, day temperatures ranged from 15° C. to 19° C. and night temperatures ranged from 14° C. to 16° C. Plants were 13 weeks old when the photographs and description were taken. In the following description, color references are made to The Royal Horticultural Society Colour Chart, 2007 Edition, except where general terms of ordinary dictionary significance are used.

Botanical classification: *Campanula portenschlagiana* 'Bkpcmpjy'.

Parentage:

*Female, or seed, parent*.—Proprietary selection of *Campanula portenschlagiana* identified as code number 4400102, not patented.

*Male, or pollen, parent*.—Proprietary selection of *Campanula portenschlagiana* identified as code number 4400293, not patented.

Propagation:

*Type*.—By cuttings.

*Time to initiate roots, summer*.—About 21 days at temperatures about 19° C. to 21° C.

*Time to initiate roots, winter*.—About 21 days at temperatures about 15° C. to 18° C.

*Time to produce a rooted young plant, summer*.—About 26 days at temperatures about 19° C. to 21° C.

*Time to produce a rooted young plant, winter*.—About 23 days at temperatures about 15° C. to 18° C.

*Root description*.—Medium in thickness, fibrous; white in color.

*Rooting habit*.—Moderately freely branching; medium density.

Plant description:

*Plant and growth habit*.—Herbaceous perennial; upright to outwardly spreading plant habit; freely branching habit with about 27 branches developing per plant; moderately vigorous growth habit.

*Plant height*.—About 11.2 cm.

*Plant width*.—About 28.2 cm.

*Lateral branch description*.—Aspect: About 80° from vertical. Length: About 11.9 cm. Diameter: About 2 mm. Internode length: About 1.5 cm. Strength: Moderately weak. Texture: Smooth, glabrous. Color: Close to 143C.

Leaf description:

*Arrangement*.—Alternate, simple.

*Length*.—About 2 cm.

*Width*.—About 2.5 cm.

*Shape*.—Reniform to orbicular.

*Apex*.—Rounded and retuse.

*Base*.—Reniform to cordate.

*Margin*.—Coarsely and irregularly dentate.

*Texture, upper and lower surfaces*.—Smooth, glabrous.

*Venation pattern*.—Pinnate.

*Color*.—Developing leaves, upper surface: Close to 137B. Developing leaves, lower surface: Close to 138B. Fully developed leaves, upper surface: Between N137A and 147A; venation, close to 143A. Fully developed leaves, lower surface: Close to 137C; venation, close to 143A.

*Petioles*.—Length: About 3.5 cm. Diameter: About 1 mm. Texture, upper and lower surfaces: Smooth, glabrous. Color, upper and lower surfaces: Close to 143A to 143B.

Flower description:

*Flower arrangement and shape*.—Single campanulate flowers arranged in axillary and terminal panicles or racemes; flowers face mostly upright to slightly outwardly; freely flowering habit with about ten flowers developing per inflorescence.

*Natural flowering season*.—Early flowering habit; plants begin flowering about 13 weeks after planting; in the garden, flowering continuous from April to September in The Netherlands.

*Flower longevity on the plant*.—About 30 days; flowers persistent.

*Fragrance*.—Faint, pleasant.

*Inflorescence height*.—About 5.7 cm.

*Inflorescence diameter*.—About 5 cm.

*Flower buds*.—Length: About 1.2 cm. Diameter: About 5 mm. Shape: Narrowly obovate. Color: Developing sepals (outer surface), close to 137B and towards the base, close to 143B; developing petals, close to 86B to 86C.

*Flower diameter*.—About 2.5 cm.

*Flower length (height)*.—About 1.5 cm.

*Petals*.—Arrangement: Five in a single whorl; lower 40% of petal length fused. Length: About 2 cm. Width, free part of the petal: About 6 mm. Shape: Narrowly oblanceolate to narrowly elliptic. Apex: Acute. Margin: Entire. Texture, upper and lower surfaces: Smooth, glabrous. Color: When opening, upper surface: Close to N87A. When opening, lower surface: Close to N86C. Fully opened, upper surface: Close to N82A; color becoming closer to N89B to N89C with development. Fully opened, lower surface: Close to N87C.

*Sepals*.—Arrangement: Five in a single campanulate whorl; lower 15% of sepals fused. Length: About 7 mm. Width, base of free part of the sepal: About 1.5 mm. Shape: Lanceolate. Apex: Narrowly acute. Margin: Entire. Texture, upper and lower surfaces: Smooth, glabrous. Color: When developing, upper surface: Close to 137B. When developing, lower surface: Close to 137B; towards the base, close to 143B. Fully developed, upper surface: Close to 137C. Fully developed, lower surface: Close to 137B; towards the base, close to 143B.

*Peduncles*.—Length: About 2.6 cm. Diameter: About 1.5 mm. Aspect: Terminal inflorescences, upright; axillary inflorescences, about 75° from stem axis. Strength: Moderately weak. Texture: Smooth, glabrous. Color: Close to 143C.

*Pedicels*.—Length: About 1.8 cm. Diameter: About 1.8 mm. Aspect: About 30° from peduncle axis. Strength: Moderately weak. Texture: Smooth, glabrous. Color: Close to 143C.

*Reproductive organs*.—Stamens: Quantity per flower: Five. Filament length: About 1 mm. Filament color: Close to NN155C. Anther length: About 5 mm. Anther shape: Lanceolate. Anther color: Close to 4C. Pollen amount: Moderate. Pollen color: Close to 4D. Pistils: Quantity per flower: One. Pistil length: About 1.1 cm. Stigma shape: Decurrent. Stigma color: Close to 76C to 76D. Style length: About 1 cm. Style color: Close to 76D. Ovary color: Close to 143C.

*Seeds and fruits*.—Seed and fruit production have not been observed on plants of the new *Campanula*.

Disease & pest resistance: Plants of the new *Campanula* have not been observed to be resistant to pathogens and pests common to *Campanula* plants.

Garden performance: Plants of the new *Campanula* have exhibited good tolerance to rain, wind and temperatures ranging from −15° C. to 30° C.

It is claimed:

1. A new and distinct *Campanula* plant named 'Bkpcmpjy' as illustrated and described.

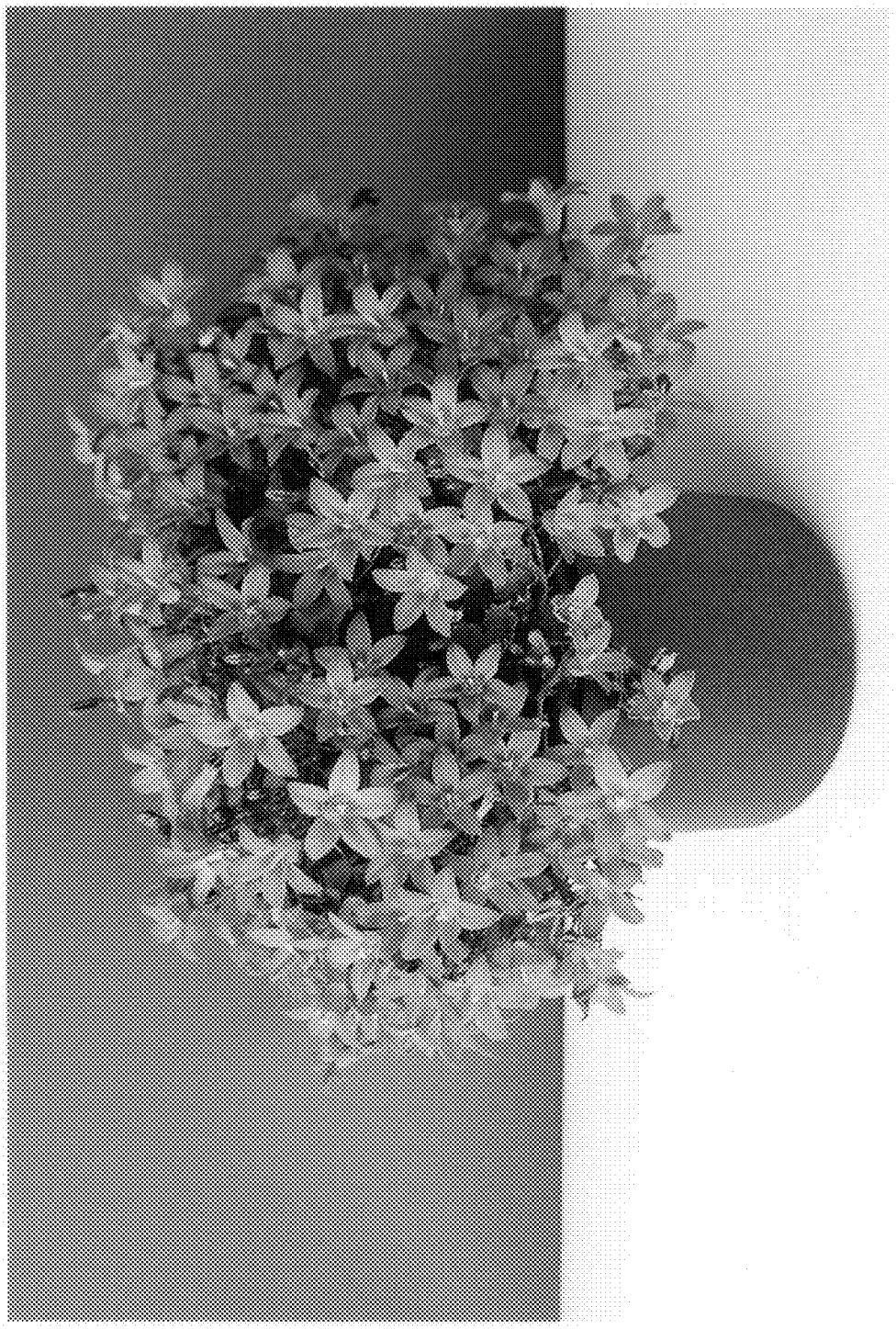

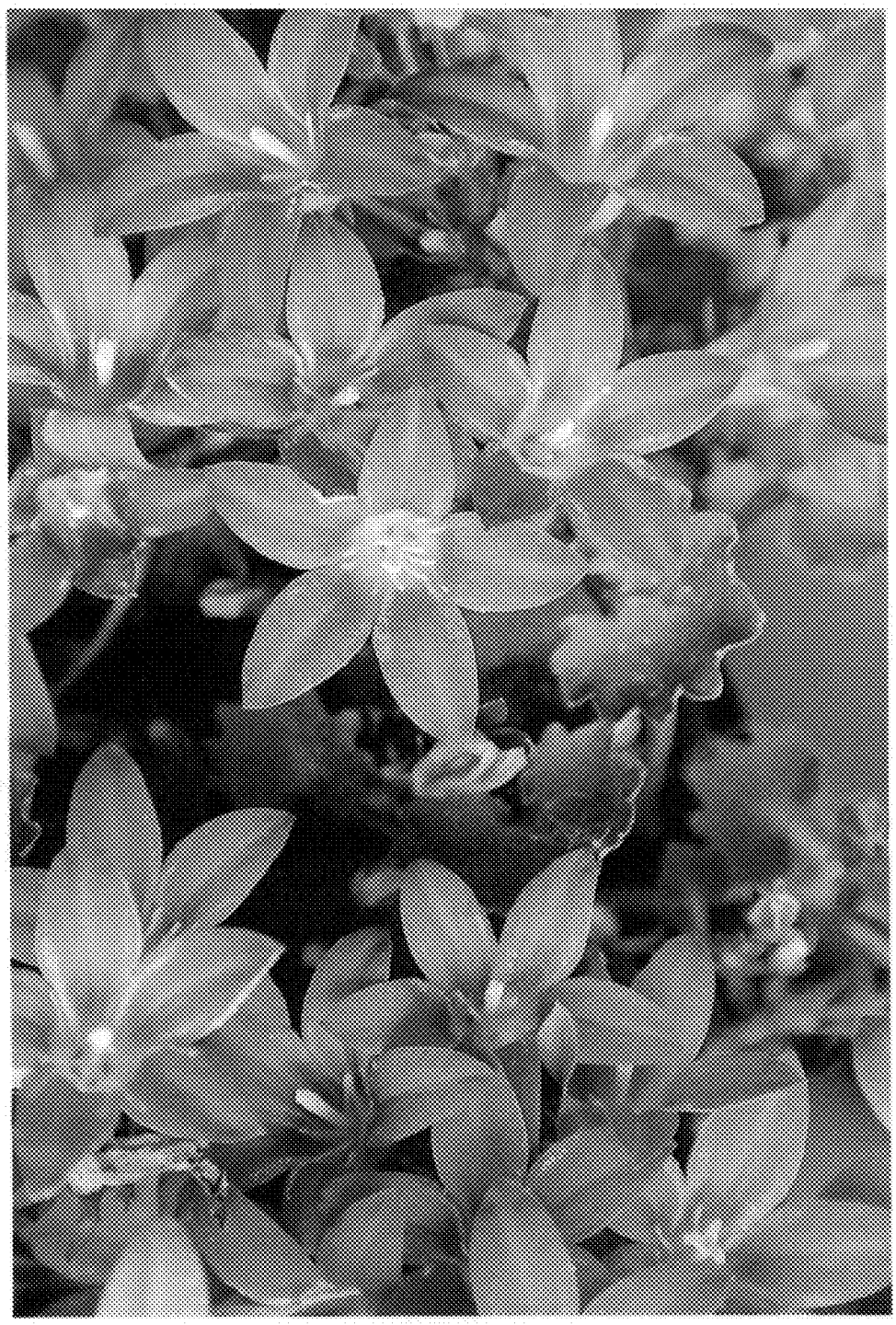

* * * * *